(12) United States Patent
Souchay et al.

(10) Patent No.: US 7,212,606 B2
(45) Date of Patent: May 1, 2007

(54) APPARATUS FOR RADIOGRAPHIC PROJECTION TOMOGRAPHY

(75) Inventors: Henri Souchay, Versailles (FR); Rémy Klausz, Neuilly sur Seine (FR); Matti Petri Jouhikainen, Järvenpää (FI)

(73) Assignee: General Electric Company, Schenectady, NY (US)

(*) Notice: Subject to any disclaimer, the term of this patent is extended or adjusted under 35 U.S.C. 154(b) by 0 days.

(21) Appl. No.: 11/180,266

(22) Filed: Jul. 13, 2005

(65) Prior Publication Data
US 2006/0078084 A1   Apr. 13, 2006

(30) Foreign Application Priority Data
Sep. 24, 2004   (FR)   ................ 04 52157

(51) Int. Cl.
*A61B 6/03* (2006.01)
(52) U.S. Cl. .................. 378/37; 378/21; 378/27
(58) Field of Classification Search .......... 378/21, 378/23, 24, 25, 37, 4, 12, 26
See application file for complete search history.

(56) References Cited

U.S. PATENT DOCUMENTS

| | | | |
|---|---|---|---|
| 3,733,487 A | 5/1973 | Louche et al. | |
| 3,824,397 A * | 7/1974 | Bauer et al. | 378/37 |
| 4,039,836 A | 8/1977 | Shaw et al. | |
| 4,304,999 A | 12/1981 | Richey et al. | |
| 4,853,540 A | 8/1989 | Nakajima | |
| 5,872,828 A * | 2/1999 | Niklason et al. | 378/23 |

FOREIGN PATENT DOCUMENTS

| | | |
|---|---|---|
| DE | 11 18 928 B | 12/1981 |
| EP | 1 428 473 A | 6/2004 |
| FR | 2352531 A | 12/1977 |
| FR | 2568122 A | 1/1986 |
| WO | WO 2004/049946 A | 6/2004 |

* cited by examiner

*Primary Examiner*—Edward J. Glick
*Assistant Examiner*—Hoon Song
(74) *Attorney, Agent, or Firm*—Cantor Colburn LLP

(57) ABSTRACT

In an apparatus for radiographic projection tomography, particularly mammography, an X-ray tube is mounted at the end of a swiveling arm, with a relative movement mechanism. The relative movement mechanism is such that it enables the tube to follow a path of a cycloid. Images or exposures taken only during the time when the tube, in its path, follows cusp points such that it is possible to keep a constant speed of movement of the arm while at the same time increasing the useful duration of an image. Vibration or oscillation effects inherent in the apparatus are compensated by the positioning, if necessary, of a counterweight.

88 Claims, 4 Drawing Sheets

APPARATUS FOR RADIOGRAPHIC PROJECTION TOMOGRAPHY

CROSS-REFERENCE TO RELATED APPLICATIONS

This application claims the benefit of a priority under 35 USC 119(a)–(d) to French Patent Application No. 04 52157 filed Sep. 24, 2004, the entire contents of which are hereby incorporated by reference.

BRIEF DESCRIPTION OF THE INVENTION

An embodiment of the present invention is an apparatus for radiographic projection tomography, and in a particular an apparatus for mammography, wherein the radiation is X-ray.

Projection tomography using X-rays is a technique that enables the acquisition of an image of a section, generally a planigraphic plane, within a body or within an object. In practice, and in medicine, a patient is subjected to an examination to identify the presence and the nature of illnesses, such as tumors, to be diagnosed or cured.

The principles of projection tomography are described in FR-A-2 568 122. This FR-A-2 568 122 discloses a mechanical type of tomography apparatus that indicates constant homothetic relationship or scaling between a plane of movement of a source of radiation, such as an X-ray tube, a plane of a detection film, and a plane of a slice to be imaged in a body to be examined.

The acquisition of such images by X-ray however presents problems inherent in the technology of X-ray production. In practice, X-ray tubes are capable of emitting radiation of a required hardness and an expected level of power only in well-controlled conditions of use. In particular, during acquisition and as and when the different images or exposures are executed, the temperature of the focal spot of the tube rises, entailing the risk of either causing damage to the anode of the X-ray tube or impairing the quality of the radiation. Furthermore, given the high power required for mammography examinations in particular, it is not possible to provide for a continuous motion of the tube with very brief exposures. The most efficient principle to be chosen then is that irradiating the object while the focal spot is immobile. Then, the focal spot is shifted between two positions of exposure. Then a consecutive image is taken and so on and so forth.

The problem encountered by this type of acquisition is firstly the amount of time for which the object, namely the patient in the case of mammography, is subjected to examination. Given that, for a mammography examination of this kind, the patient's breast is subjected to painful compression, the degree of comfort in the examination is at an unacceptable level if this examination is too lengthy. Furthermore, the weight of an X-ray tube is such that its successive shifts and stops prompt oscillations in the structure of the mammography apparatus or more generally the tomography apparatus. These oscillations have the consequence of making the focal spot tremble during the acquisition of the image. Under these conditions, the acquired image is fuzzy and cannot be exploited. It then becomes necessary to find a compromise between these difficulties. On the one hand, if it is sought to prevent the oscillations or swiveling of the tomography apparatus between the images, the duration of the examination is stretched to the detriment of the patient's comfort. On the other hand, if it is sought to accelerate the succession of images, the image obtained is not of good quality. In any case, the compromise is not satisfactory.

BRIEF DESCRIPTION OF THE INVENTION

An embodiment of the invention is a radiographic projection tomography apparatus comprising means for support, particularly to support an object to be subjected to tomography; means for providing a source of radiation, such as a tube provided with an X-ray emitting focal spot; means for detecting, such as an X-ray detector to detect X-rays emitted during an exposure of the object; means for shifting the X-ray tube, along a path relative to the support, the means for shifting comprising means for ordering such that the speed of a focal spot of the tube varies as a function of the position of this focal spot relative to the support, wherein the means for ordering provides for the acceleration of the focal spot relative to the support is continuous, provides for the speed of the focal spot relative to the support is continuous, provides for a multiplicity of positions distributed on this path, the number of which is greater than or equal to three, the speed passes each time through a minimum value at a point, and provides for each exposure of the object to the X-rays is made for a duration in which the speed of the focal spot is minimal.

An embodiment of the invention is a radiographic projection tomography apparatus comprising means for support, particularly to support an object to be subjected to tomography; means for providing a source of radiation, such as a tube provided with a X-ray emitting focal spot; means for detection, such as an X-ray detector to detect X-rays emitted during an exposure of the object; means for carrying the focal spot, such as mobile arm, along a path relative to the means for support during a tomography operation, wherein the means to carry the focal spot comprises means for prompting a relative shift of the focal spot with respect to one end of the arm, or comprises means for modifying a mean orientation of irradiation of the tube relative to an envelope of the tube, during the tomography operation.

BRIEF DESCRIPTION OF THE DRAWINGS

An embodiment of the invention will be understood more clearly from the following description and the accompanying figures. These figures are given only by way of an indication and in no way restrict the scope of the invention. Of these figures.

DETAILED DESCRIPTION OF THE INVENTION

Figure 1:
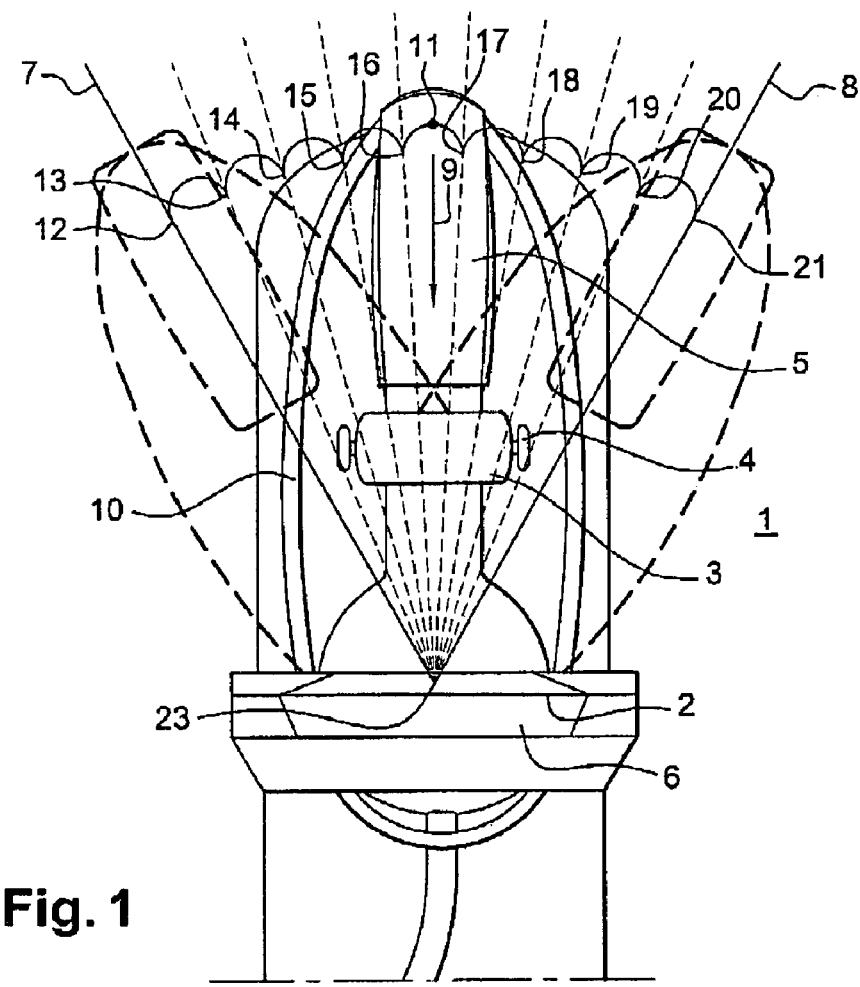
FIG. 1 is a diagrammatic view of the radiographic projection tomography apparatus, particularly a mammography apparatus.

FIG. 1 shows a radiographic projection tomography apparatus 1 according to an embodiment of the invention. The tomography apparatus 1 has a means for support 2 to support an object that has to be subjected to tomography. In an embodiment of the invention, the tomography apparatus can be a mammography apparatus wherein the means for support 2 is a breast-holder tray to support a patient's breast. Nevertheless, any other type of tomography apparatus can be envisaged. Normally, the patient's breast is placed on the tray 2 and compressed by a pad 3 which can be maneuvered by an operator using for example handles 4. The tomography device 1 furthermore comprises a source of radiation, such as an X-ray emitting tube 5 and means for detection, such as a detector 6 capable of detecting the rays after they have crossed the patient's breast. The detector 6 is placed beneath the breast-holder tray 4. In practice, the pad 3 is made of an X-ray transparent material, plastic in particular.

While the pad 3, the patient's breast, the tray 2 and the detector 6 are in fixed positions, the X-ray tube 5 may take up several positions in space relative to this assembly. In particular, FIG. 1 shows distributed in reorientation between a first extreme position 7 and a second extreme position 8 that are, for example, symmetrical relative to each other relative to a bisecting direction 9. The positions are on the whole distributed on an arc of a circle. To this end, an arm 10, herein formed by a hoop, carries the tube 5. However, it is possible to envisage the making, at the top of the tomography apparatus 1, of a horizontal rail (for example fixed to a ceiling) to support an arm for holding the X-ray tube 5 in a sliding position. In this case, the path of the X-ray tube 5 would be situated on the whole in a plane rather than being situated, at the end of the hoop 10, on the whole on an arc of a circle. There are other possible arrangements enabling the tube to shift in a plane or a sphere portion.

The tube 5 is provided with a focal spot 11 that is the X-ray emitting focal spot. According to an embodiment of the invention, the speed of the focal spot 11 varies according to the position of this focal spot 11 relative to the support 2. The essential characteristics of the variation in speed are that the acceleration of the focal spot 11 relative to the support 2 is continuous. The value of this speed therefore undergoes continuous variation. Similarly, the speed of the focal spot 11 relative to the support is also continuous. For a multiplicity of exposure positions, herein represented by ten positions numbered 12 to 21, the number of these positions being greater than or equal to 3, the speed passes each time through a minimum value at only one point. The number of exposure positions, which is greater than or equal to 3, is related to the fact that there is a known way of arranging a mammography device whose tube is at a halt at the incidence (position) 7 and, after regular exploration, is also at a halt at the incidence (position) 8.

Figure 2A:
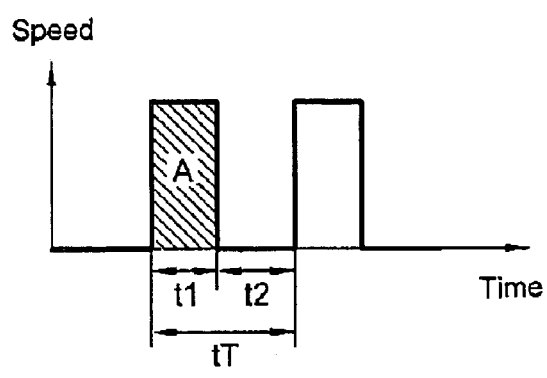
FIGS. 2a and 2b are theoretical and practical views respectively of the speed chart of the focal spot in the state of the art.

On the path, the positions are distributed, preferably evenly, even though, with the image reconstruction processing corrections, it would be possible to envisage a case where the positions 12 to 21 are not evenly distributed. The exposure of the object interposed in the path of the X-rays is done during the periods when the speed of the focal spot is minimal, i.e. in and around the positions 12 to 21. As can be seen in FIG. 1, especially when the motion of the focal spot is cycloid, the exact path of the focal spot is not necessarily that of an arc of a circle or of a sphere portion but is inscribed in a circular or spherical ring portion. However, the cycloid motion could be made in a plane or on a sphere portion. In this case, the relative motion would be tangential to this plane or to the surface of this sphere FIG. 2a shows that, in the state of the art, the speed of the focal spot 11 should have a nominal value during a period t1 and lead the focal spot 11 to travel a distance A during this period t1. During a period t2 following this period t1, the X-ray tube 5 is stopped, the focal spot 11 is immobile and the image can be taken. Thus, continuing in this way, several images can be taken while the tube is placed with the hoop arm 10 at several positions along its path. However, since the speeds represented in FIG. 2a undergo infinite variations when they are set up and when they are eliminated, this solution is not possible in practice.

Figure 2B:
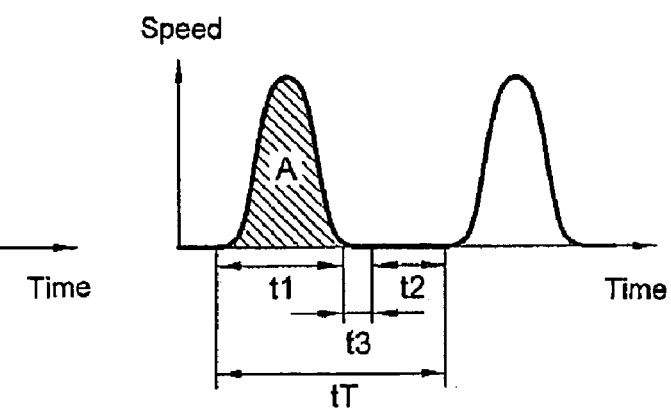

As shown in FIG. 2b, the speed chart can be corrected so that the variation in speed is mechanically possible, increasing at the beginning of the period t1 and then decreasing at the end of the period t1. In practice, before the period t2 during which the image is taken, it is necessary to wait for a waiting period t3 that served as a period for the damping of the oscillations. In these conditions, even for a short period t2, for example of about 50 milliseconds, the total duration tT to make an image and move to the next one was very great, in the range of 700 milliseconds. For a large number of images, for example a number greater than about ten, the duration of the examination could thus go up to about 10 seconds. This is unbearable for the patient whose breast is being compressed.

In an embodiment of the invention, to obtain the recommended speed chart in practice the mobile arm 10 bearing the focal spot 11 along the path is provided with means for carrying and shifting the focal spot 11 relative to one end of the arm. In other words, the arm 10 undergoes a continuous movement, which may be at constant speed along a path or at least a speed with a low variation. In one example, the path of the arm 10 and especially its end 49 (FIG. 5a) will be an arc of a circle or situated on a sphere portion. If the arm 10 is hooked to a rail, its path is located in a plane. With respect to this end of the arm 10 to which the X-ray tube 5 is attached, a relative motion is then provided, during the tomography operation, so that the focal spot 11 is sometimes driven at very high speed and sometimes driven by very low speed. The speed passes each time through a minimum value at only one point. Images are taken during the period when this speed of the focal spot is thus minimal.

Figure 3A:
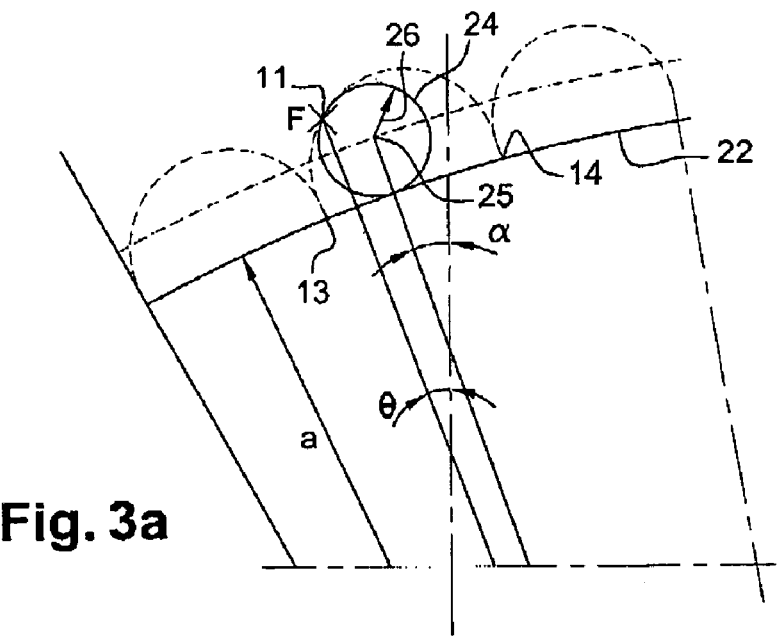
FIGS. 3a and 3b show an example of an embodiment of the invention in which a movement of the focal spot by which it is possible to obtain a favorable speed chart.

In one example, FIG. 3a shows a path 22 of the end 49 in the form of an arc of a circle. This path is centered on a center of aim 23 (as shown in FIG. 1, placed approximately in the vicinity of or in the middle of the detector 6). In practice, the center of aim 23 may be placed at the place in which the main tomography section is situated. However, given the corrections that can be made, this constraint however is not necessary. During its shift, the end 49 of the arm 10 therefore occupies an x-axis position on its path 22. Relative to these x-axis positions, the focal spot 11 is shifted. In one example, shown simply in FIG. 3a, the focal spot 11 is placed in correspondence with the periphery of a circle 24 that rolls without slip on the path 22. In these conditions, the focal spot 11 undergoes a cycloid trajectory, in this case an epicycloid path.

Figure 3B:
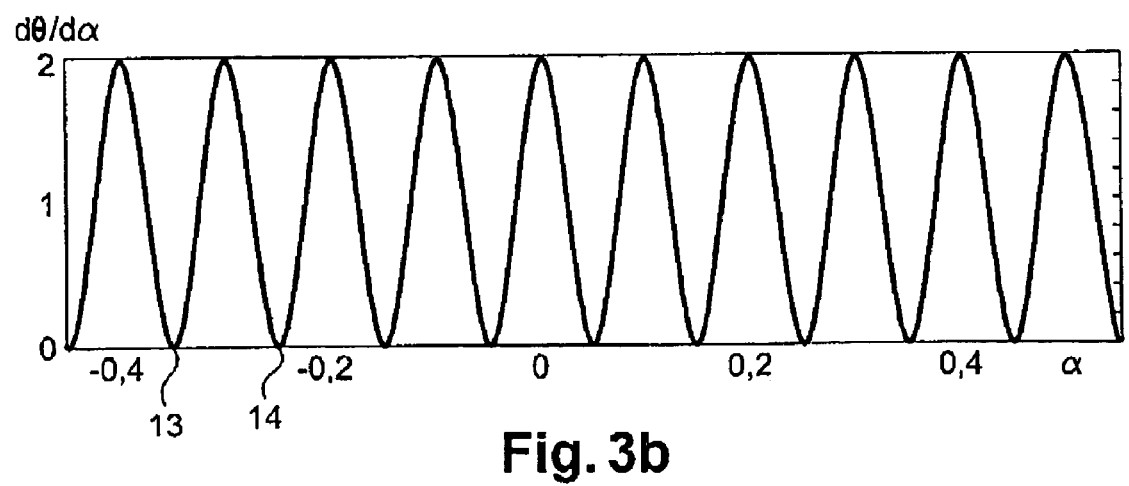

Angles respectively α and θ are used to mark the positions of the center 25 of the circle 24 and of the focal spot 11. FIG. 3b shows the development of the relative variation of the angular speed of the focal spot 11 relative to the angular speed of the center 25 at the function of the angular position of this center 25. This variation is a sine variation. It shows that, at the cusp points such as 13 and 14 of the cycloid motion, the relative speed of the focal spot 11 with respect to this center 25 is zero whereas it is very high between these cusp points.

The representation of FIG. 3a corresponds to a case where the focal spot is placed on or in correspondence with a circle 24 which itself rolls without slip on the path 22. However, it can be planned to place the focal spot below or above the precise value of the radius 26 of the circle 24. If it is placed below or above this value, the curve of FIG. 3b changes shape. These solutions generally bring no significant improvements, except on the margins, or are even less optimal than the one in which the focal spot is located on the periphery of the circle 24.

Figure 4A:
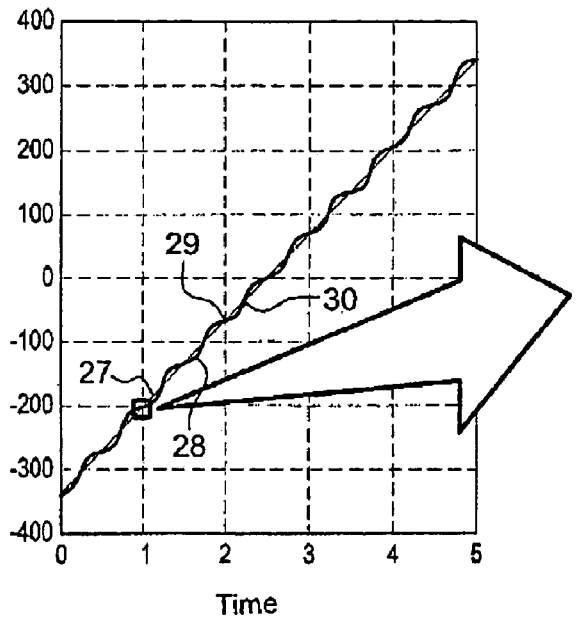
FIGS. 4a and 4b are comparative curves of positions in space of the focal spot, as a function of time, along its path, respectively in the state of the art and in an embodiment of the invention.

FIG. 4a shows the linear progress in time (curve 27) of the position of the center 25 of the circle 24. For a constant mean speed, the curve 27 is a straight line developing linearly in time. FIG. 4a overlooks the parts of this progress corresponding to the putting into speed, at constant speed, of the center 25 and hence of the arm 10 that carries the X-ray tube 5, which itself contains the focal spot 11. The curvilinear x-axis values on the path 22 are indicated on the y-axis. The same figure also shows the curve 28 representing the progress of the curvilinear x-axis value of the projection of the focal spot 11 on the path 22. The projection is the one along θ.

Just as the curve 27 takes the form of a straight line, so the curve 28 takes the form of an oblique-based sine curve. This sine curve has horizontal or almost horizontal parts 29, and vertical or almost vertical parts 30. The parts 29 correspond to periods during which the exposures or images are taken. In these periods, the focal spot 11 moves little as a function of time. The periods 30 are the periods during which the X-ray tube 5 no longer irradiates any object, where the exposure or image has not been taken, and during which, on the contrary, the focal spot 11 moves at high speed.

Figure 4B:
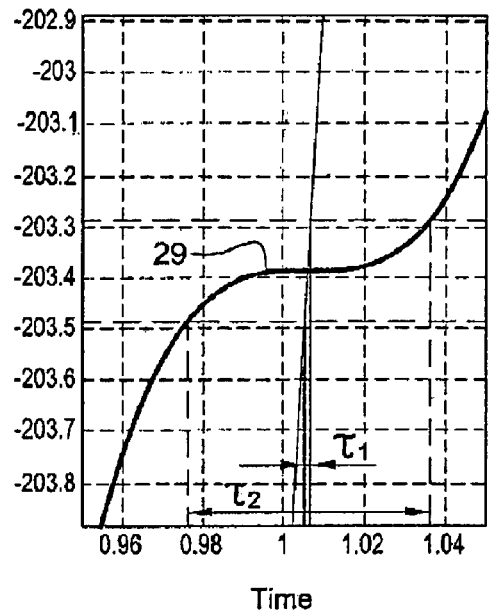

FIG. 4b shows a magnified view of the progress of the center 25 and of the focal spot 11. Assuming that the taking of an exposure, the image, can be done while the focal spot moves by 200 micrometers around a mean position, it is observed that, for a given mean speed and, if the focal spot were to be placed at the center of the circle 25, the duration of an exposure authorized by an even speed would be $\tau 1$, equal in one example to 1.5 milliseconds. Such a mean speed leads to a total scan of the exploration zone of about one to three seconds, which is bearable for the patient. By comparison, owing to the presence of the slowing-down phases 29, with the cycloid path of the focal spot 11, the possibly duration for the exposure becomes $\tau 2$, in the range of 60 milliseconds, FIG. 4b. In other words, an embodiment of the invention makes it possible to obtain sufficient irradiation with an X-ray tube 40 times less powerful than a tube that it would have been necessary to implement in the case of linear variation. Besides, it may be impossible to make such a tube.

Figure 5A:
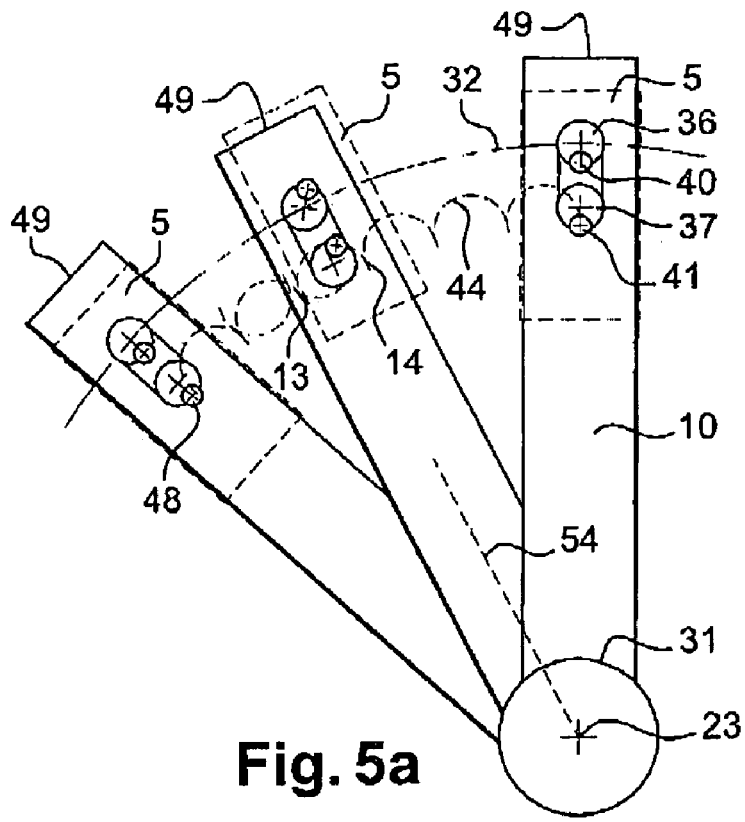
FIGS. 5a and 5b show features of an embodiment of the invention.
Figure 5B:
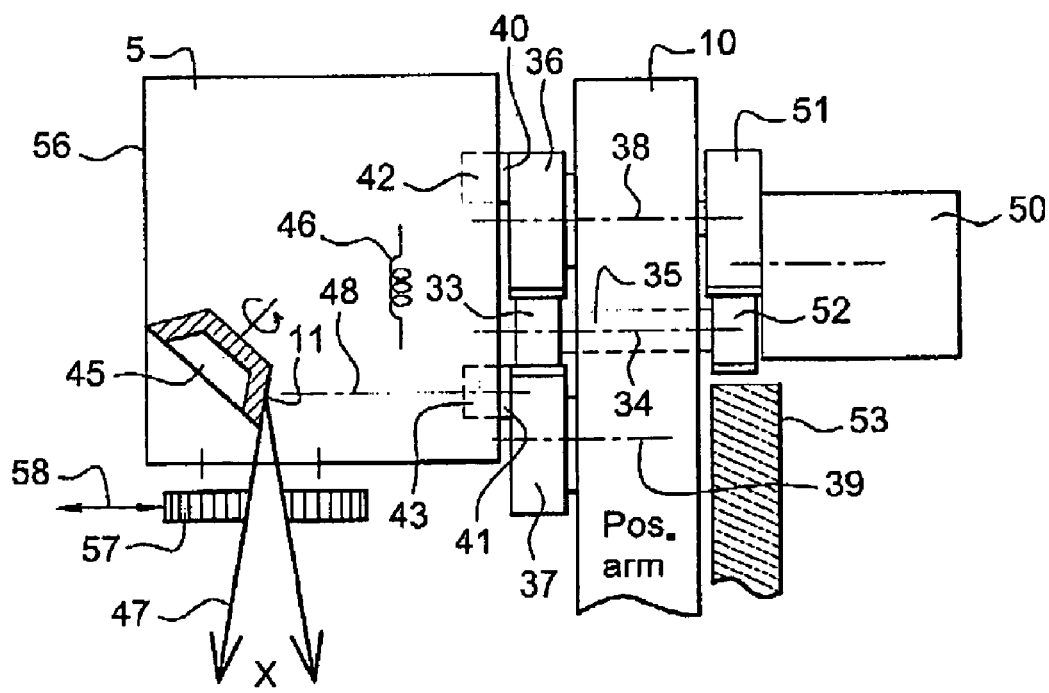

FIG. 5a shows an exemplary embodiment of an apparatus enabling a cycloid motion. With respect to a center of rotation 23, corresponding to the center of aim of the tube 1, the figure shows an arm 10. The arm 10 is capable of tilting, by means of a bearing 31, about the center 23. All the points of the arm 10 are therefore subjected to circular shifts, whose center is that of an arc of a circle 32. As can be seen in FIG. 5b, arm 10 carries a toothed wheel 33 that has an axis of rotation 34 and is supported by a bearing 35. The toothed wheel 33 drives two toothed wheels respectively 36 and 37, with an axis of rotation respectively 38 and 39, parallel to the axis 34. The axes 38 and 39 are furthermore positioned symmetrically to one another relative to the position of the axis 34. The two-toothed wheels 36 and 37 are also shown in FIG. 5a. Shafts corresponding to the axes 38 and 39 are also held by bearings, not shown herein, and maintained by the arm 10.

The toothed wheel 33 is driven by a motor, not shown, whose angular position is indexed to the position in rotation of the arm 10 about the center 23. The two-toothed wheels 36 and 37 each carry an off-centered pin, 40 and 41 respectively. The pins 40 and 41 are circular cylindrical with an axis of the circular cylinder parallel to the axes 34, 38 and 39. These pins, as shown in FIG. 5b, are engaged in housings, respectively 42 and 43 made in an envelope of the tube 5. The pins 40 and 41 furthermore hold the tube 5, for example by means of circular grooves.

When the arm 10 rotates about the center 23, the axis 34 rotates on itself and drives the two-toothed wheels 36 and 37 so that both rotate in the same sense (because their axes 38 and 39 are symmetrical with the axis 34). The pins 40 and 41 then undergo a cycloid motion. Here, we have shown the epicycloid trace 44, FIG. 5a, of the position of the axis of the pin 41.

In the tube 5, a rotating anode 45 is placed before the cathode 46 that bombards it with electrons. Subjected to this bombardment, the anode 45 is the site, at the position of its focal spot 11, of an X-ray emission 47. Here, the focal spot 11 is in the extension of an axis 48 of the pins 41 set up on the periphery of the wheel 37. The focal spot 11 therefore undergoes all the motions of this axis 48.

FIG. 5a shows that, relative to the end 49 of the arm 10 (or relative to any point whatsoever of this arm 10), the tube 5 and therefore its focal spot 11 undergo epicycloid shifts. The shift could have been hypocycloid. However, in this case, it would have had the drawback of being less interesting since, during fast shifts, the tube would have been brought closer to the center 23. It would have been moved away from the center during the shots. For this reason, the epicycloid solution is preferable to the hypocycloid solution.

As can be seen in FIG. 5a, the tube 5, which may weigh up to about 10 kg. exerts fairly strong reaction forces on the bearing 31. With a very tight mechanical construction, the accelerations, resulting especially from the turns at the cusp points, and from the high speeds of tangential movement, can be contained. However, to facilitate construction, place a counterweight 50 on the other side of the arm 10 relative to the one in which the tube 5 is placed. The counterweight 50 is also driven by a toothed wheel 51 itself driven by a toothed wheel 52. The wheel 51 and the toothed wheel 52 rotate in the same sense, and the same axes 38 and 35, respectively as the toothed wheels 36 and 33. However, the position at which the counterweight 50 is attached to the wheel 51, for example by a pin, is also off-centered and diametrical, relative to the axis 38, with respect to the position at which the pin 40 is located. In practice, the counterweight 50 undergoes an epicycloid motion offset from that of the tube 5. In this way, the counterweight 50 compensates for the reactions imposed on the bearing 31.

The arm 10 carries the tube 5. If, instead of an arm 10 swiveling about an axis 23, it had been chosen to use a slide or carriage sliding on a rail as in the state of the art, then a shaft maintained on this carriage would have carried the tube and it is with respect to this shaft fulfilling the role of an arm that the relative shift of the focal spot would have been measured.

To index and drive the position of the toothed wheel 33 in rotation on the arm 10, the wheel will engage in a toothed circular track 53 forming an arc of a circle whose center is 23. In this case, the track 53 is held rigidly relative to the structure of the mammography device 1 and especially relative to the support and the detector 6. The pins 40 and 41 are preferably held up at the periphery of the wheels 36 and 37 respectively.

When the two wheels 36 and 37 are taken along in rotation simultaneously, pins 40 and 41 are always aligned with each other along a direction parallel to a direction 54 of the median axis of the arm 10. The two housings are aligned along the main direction of radiation of the tube. This mode of action gives a result wherein the main direction of the tube 5 is always oriented toward the center 23. Otherwise, a pantograph device could be planned to control the alignment.

FIG. 5*b* also shows that the X-rays 47 pass through a window 55 made in an envelope 56 of the tube. Downstream from the window 55 (or even upstream), a slit of a multi-leaf collimator 57 makes it possible, by action on the leaves along the directions 58, to limit the spread of the radiation 47.

Figure 6:
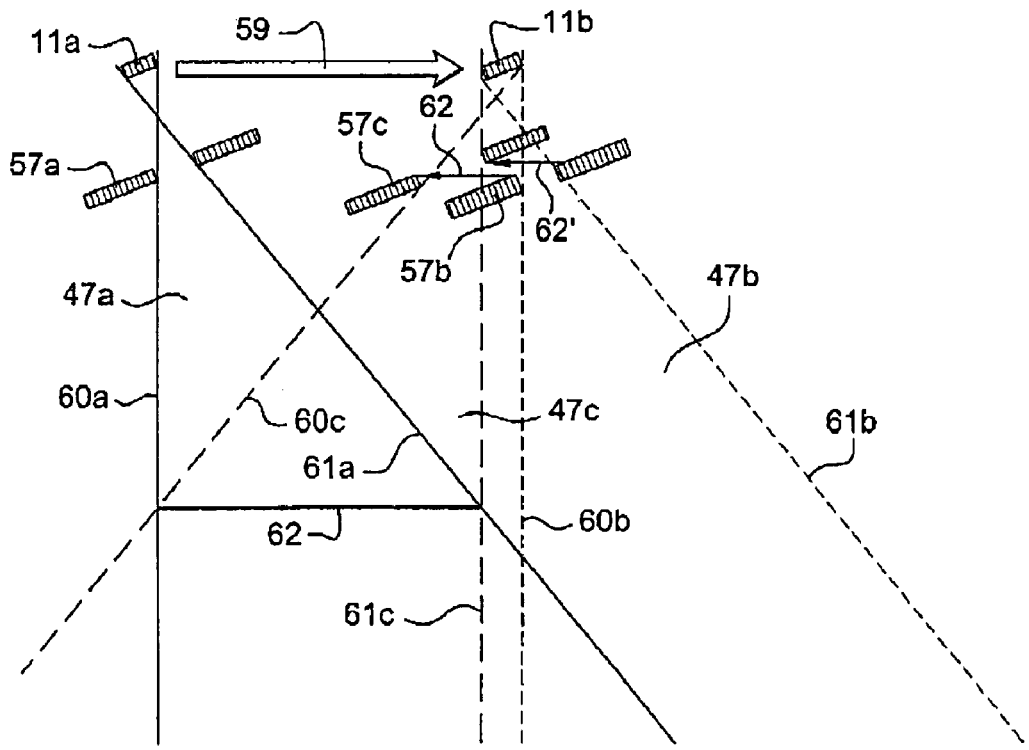
FIG. 6 is a presentation of a variant embodiment of the invention.

In another embodiment of the invention as shown in FIG. 6, a multi-leaf collimator 57 is used to shift the focal spot in a direction opposite to that of the motion of the tube 5 during the exposure or imaging. For example, at the start of the imaging, the focal spot 11 is in the position 11*a*. During the imaging, it moves, in the direction indicated by the arrow 59 up to the position 11*b*. In the position 11*a*, the collimator leaves are, spatially, in the position 57*a*, while the X-radiation is, spatially, in the position 47*a*. A mean direction of irradiation of the tube 5 is contained, in this case, spatially, between the boundaries 60*a* and 61*a* of the lateral X-rays blocked at the edge of the slot by the leaves of the collimator 57.

In position 11*b*, while the focal spot has shifted in space, the radiation would ordinarily be located at 47*b* between the boundaries 60*b* and 61*b*, represented by short dashes. Radiation 47*b* would then be defined by leaves of the collimator in the position 57*b*. Instead, in an embodiment of the invention, the leaves of the collimator are subjected to the shifts 62 and 62' whose direction is opposite that of the shift 59. In these conditions, the useful radiation proves to be the radiation 47*c*, whose mean direction is located between the lateral rays 60*c* and 61*c* represented by long dashes. Consequently, while the tube has shifted from the position 11*a* to the position 11*b*, a same zone 62 of the object has been irradiated. In this manner, a mean orientation of irradiation of the tube is modified relative to the envelope 56 of the tube during the exposure or imaging. Naturally, after the exposure or imaging has been made, and while the envelope continues to shift, the leaves return to the position 57*a* in anticipation of an exposure in the imminent future.

It is possible, particularly when using an electronic type of detector (without film), to shift the X-ray tube so that it is no longer in a plane parallel to the plane of the detector and to the plane of the section to be imaged, but on an arc of a circle or even on a sphere portion. In this case, the distortions of an acquired image are corrected accordingly. In practice then, rather than a radiosensitive film, an electronic detector is used and, from a signal measured by the detector and converted into a digital signal all the corrective processing operations necessary to reconstruct the images are performed.

Rather than acquire an image by continuous integration of the irradiation on an X-ray sensitive film, it is therefore preferred to proceed by a sampling of a series of images. The object and therefore the detector are irradiated during consecutive images or exposures. For these images or exposures, a focal spot of the X-ray tube occupies fixed positions in space that are angularly distributed. In one example, and although this cannot be considered to be a limitation, the angular exploration will thus be equal to 60 degrees, plus or minus 30 degrees relative to a median direction of irradiation, which is generally vertical for a mammography.

Doing this acquisition, a certain number of images are acquired, for example nine, eleven, thirteen or another number of images depending on the desired precision of the image reconstruction. By then applying image reconstruction algorithms, of the type used in computed tomography, it is possible to reconstruct the image in a planigraphic plane, as well as to reconstruct other images in planes adjacent to this planigraphic plane. Thus, it is possible to speak of synthesis tomography in which all the images are acquired in a single scan. In practice, the image in the planigraphic plane is more precise than the images in the adjacent planes when the exploration is not made over 180°. The corrections implied by the synthesis relate as much to the fact that the path of the focal spot of the X-ray tube is not homothetic relative to the position of the detector as to the fact that, depending on the different values of incidence, the detector shows a tilt relative to the normal direction of projection. The effects of these acquisition constraints can be corrected by computation to use computed tomography reconstruction algorithms.

An embodiment of the invention, provides a system for the acquisition of discrete images during which the speed of movement of the focal spot is very low, while it continues to develop during the images, without reaching a sustained halt. With this mode of action, it is somewhat possible to reduce the effects of the decelerations and accelerations corresponding to each image, so as to reduce the trembling. For a same mean speed of the shift of the focal spot during the total exploration in keeping with an examination that is acceptable to the patient, this mode of action enables an increase in the duration of the images, for a same tolerable shift during the acquisition of each image. This increase in duration is in a proportion of 40 times the duration of an image corresponding to a constant maintaining of the speed of shift of the focal spot.

In this constant development of the speed it is also possible to compensate for the oscillations relative to the first-order harmonic values of the motion. In one embodiment, the compensation is mechanical.

In another embodiment, the law of speed thus imposed can be complied with through the use of an optical encoder, with feedback control or open loop control, such as for example, as disclosed in FR-A-2 568 122.

Another embodiment causes a shift of the focal spot mechanically, relative to one end of an arm that carries the X-ray tube. In a particular example of an embodiment, this relative shift of the focal spot with respect to the end of the arm will be a cycloid, epicycloid or hypocycloid movement.

In another embodiment, the focal spot of the tube is shifted in a direction opposite the motion of the tube during the imaging. In practice, in a wall of the tube, a collimation slit is shifted in an X-ray outlet window. In this way, despite the shifting of the envelope of the tube during an image, a (temporarily) stationary state of the focal spot is brought about. More exactly in this case the mean axis of irradiation is oriented, at least approximately, to a particular fixed point in the object, for example a midpoint. If need be, the cycloid motion and the shifting of the collimator are combined. By acting in this way, the focal spot of the tube is temporarily kept in a stationary state.

Additional embodiments for achieving the same result are possible with link-rod type arrangements. A link-rod system converts a rotational motion into an alternating translation motion. Otherwise, any indexing device, with optical encoding for example, as described in the above FR-A-2 568 122, is possible.

In addition, while an embodiment of the invention has been described with reference to exemplary embodiments, it will be understood by those skilled in the art that various changes may be made and equivalents may be substituted for elements or features thereof without departing from the scope of the invention. In addition, many modifications may be made to adapt a particular situation or material to the teachings of the embodiments of the invention without departing from the essential scope thereof. Therefore, it is intended that the invention not be limited to the particular embodiment disclosed as the best mode contemplated for carrying out this invention, but that the invention will include all embodiments falling within the scope of the appended claims. Moreover, the use of the terms first, second, etc. do not denote any order or importance, but rather the terms first, second, etc. are used to distinguish one element, feature or item from another. Furthermore, the use of the terms a, an, etc. do not denote a limitation of quantity, but rather denote the presence of at least one of the referenced element, feature or item.

What is claimed is:

1. A tomography apparatus comprising:
    means for support of an object to be subjected to tomography;
    means for providing and carrying a source of radiation having a focal spot;
    means for detecting the radiation; and
    means for shifting the means for providing a source of radiation along a path relative to the means for support, the means for shifting comprising means for varying the speed of the focal spot as a function of the position of the focal spot relative to the means for support, wherein the means for shifting provides for the acceleration of the focal spot relative to the means for support is continuous and provides for the speed of the focal spot relative to the means for support is continuous and provides for a multiplicity of positions distributed on the path, the number of which is greater than or equal to three, and provides for the speed passing each time through a minimum value at a point, and provides for each exposure of the object to the radiation is made for a duration in which the speed of the focal spot is minimal.

2. The apparatus according to claim 1 wherein the means for carrying comprises means for prompting the relative shift, which causes relative motion that is cycloid, epicycloid or hypocycloid.

3. The apparatus according to claim 2 wherein the means for prompting the relative shift comprises means for motion mounted at the end of the means for carrying and provided with an off-centered pin, a position in rotation of the means for motion being indexed to a position of the means for carrying, the pin being engaged in a housing of the means for providing a source of radiation and driving the means for providing a source of radiation in motion relative to the end of the means for carrying.

4. The apparatus according to claim 3 wherein the pin is circular cylindrical with an axis set up on the periphery of the means for motion.

5. The apparatus according to claim 3 wherein the means for prompting the relative shift comprises two motion wheels mounted at the end of the means for carrying, each being provided with an off-centered pin, the positions in rotation of the two wheels being identically indexed on a position of the means for carrying, the pins being engaged in two housings of the means for providing a source of radiation, the two housings being aligned in a main direction of radiation of the means for providing a source of radiation.

6. The apparatus according to claim 4 wherein the means for prompting the relative shift comprises two motion wheels mounted at the end of the means for carrying, each being provided with an off-centered pin, the positions in rotation of the two wheels being identically indexed on a position of the means for carrying, the pins being engaged in two housings of the means for providing a source of radiation, the two housings being aligned in a main direction of radiation of the means for providing a source of radiation.

7. The apparatus according to claim 5 wherein the two motion wheels are driven by a same driving wheel.

8. The apparatus according to claim 6 wherein the two motion wheels are driven by a same driving wheel.

9. The apparatus according to claim 1 comprising a counterweight mechanism to balance the relative motion of the means for providing a source of radiation.

10. The apparatus according to claim 2 comprising a counterweight mechanism to balance the relative motion of the means for providing a source of radiation.

11. The apparatus according to claim 3 comprising a counterweight mechanism to balance the relative motion of the means for providing a source of radiation.

12. The apparatus according to claim 4 comprising a counterweight mechanism to balance the relative motion of the means for providing a source of radiation.

13. The apparatus according to claim 5 comprising a counterweight mechanism to balance the relative motion of the means for providing a source of radiation.

14. The apparatus according to claim 6 comprising a counterweight mechanism to balance the relative motion of the means for providing a source of radiation.

15. The apparatus according to claim 7 comprising a counterweight mechanism to balance the relative motion of the means for providing a source of radiation.

16. The apparatus according to claim 8 comprising a counterweight mechanism to balance the relative motion of the means for providing a source of radiation.

17. The apparatus according to claim 9 wherein the counterweight mechanism comprises a balancing wheel mounted at the end of an arm for supporting the source of radiation and provided with an off-centered means driving a counterweight, the positions in rotation of a motion wheel and of the balancing wheel being indexed in phase opposition to a position of the means for carrying.

18. The apparatus according to claim 10 wherein the counterweight mechanism comprises a balancing wheel mourned at the end of an arm for supporting the source of radiation and provided with an off-centered means driving a counterweight, the positions in rotation of a motion wheel and of the balancing wheel being indexed in phase opposition to a position of the means for carrying.

19. The apparatus according to claim 11 wherein the counterweight mechanism comprises a balancing wheel mounted at the end of an arm for supporting the source of radiation and provided with an off-centered means driving a counterweight, the positions in rotation of a motion wheel and of the balancing wheel being indexed in phase opposition to a position of the means for carrying.

20. The apparatus according to claim 12 wherein the counterweight mechanism comprises a balancing wheel mounted at the end of an arm for supporting the source of radiation and provided with an off-centered means driving a counterweight, the positions in rotation of a motion wheel and of the balancing wheel being indexed in phase opposition to a position of the means for carrying.

21. The apparatus according to claim 13 wherein the counterweight mechanism comprises a balancing wheel mounted at the end of an arm for supporting the source of radiation and provided with an off-centered means driving a counterweight, the positions in rotation of a motion wheel and of the balancing wheel being indexed in phase opposition to a position of the means for carrying.

22. The apparatus according to claim 14 wherein the counterweight mechanism comprises a balancing wheel mounted at the end of an arm for supporting the source of radiation and provided with an off-centered means driving a counterweight, the positions in rotation of a motion wheel and of the balancing wheel being indexed in phase opposition to a position of the means for carrying.

23. The apparatus according to claim 15 wherein the counterweight mechanism comprises a balancing wheel mounted at the end of an arm for supporting the source of radiation and provided with an off-centered means driving a counterweight, the positions in rotation of a motion wheel and of the balancing wheel being indexed in phase opposition to a position of the means for carrying.

24. The apparatus according to claim 16 wherein the counterweight mechanism comprises a balancing wheel mounted at the end of an arm for supporting the source of radiation and provided with an off-centered means driving a counterweight, the positions in rotation of a motion wheel and of the balancing wheel being indexed in phase opposition to a position of the means for carrying.

25. The apparatus according to claim 1 wherein to modify a mean orientation of irradiation of a source of radiation relative to an envelope of the means for providing a source of radiation, during the tomography operation, a position of a collimator slit is modified in a direction opposite that of the motion of the means for providing a source of radiation.

26. The apparatus according to claim 2 wherein to modify a mean orientation of irradiation of a source of radiation relative to an envelope of the means for providing a source of radiation, during the tomography operation, a position of a collimator slit is modified in a direction opposite that of the motion of the means for providing a source of radiation.

27. The apparatus according to claim 3 wherein to modify a mean orientation of irradiation of a source of radiation relative to an envelope of the means for providing a source of radiation, during the tomography operation, a position of a collimator slit is modified in a direction opposite that of the motion of the means for providing a source of radiation.

28. The apparatus according to claim 4 wherein to modify a mean orientation of irradiation of a source of radiation relative to an envelope of the means for providing a source of radiation, during the tomography operation, a position of a collimator slit is modified in a direction opposite that of the motion of the means for providing a source of radiation.

29. The apparatus according to claim 5 wherein to modify a mean orientation of irradiation of a source of radiation relative to an envelope of the means for providing a source of radiation, during the tomography operation, a position of a collimator slit is modified in a direction opposite that of the motion of the means for providing a source of radiation.

30. The apparatus according to claim 6 wherein to modify a mean orientation of irradiation of a source of radiation relative to an envelope of the means for providing a source of radiation, during the tomography operation, a position of a collimator slit is modified in a direction opposite that of the motion of the means for providing a source of radiation.

31. The apparatus according to claim 7 wherein to modify a mean orientation of irradiation of a source of radiation relative to an envelope of the means for providing a source of radiation, during the tomography operation, a position of a collimator slit is modified in a direction opposite that of the motion of the means for providing a source of radiation.

32. The apparatus according to claim 8 wherein to modify a mean orientation of irradiation of a source of radiation relative to an envelope of the means for providing a source of radiation, during the tomography operation, a position of a collimator slit is modified in a direction opposite that of the motion of the means for providing a source of radiation.

33. The apparatus according to claim 17 wherein to modify a mean orientation of irradiation of a source of radiation relative to an envelope of the means for providing a source of radiation, during the tomography operation, a position of a collimator slit is modified in a direction opposite that of the motion of the means for providing a source of radiation.

34. The apparatus according to claim 1 wherein the path is circular or straight.

35. The apparatus according to claim 2 wherein the path is circular or straight.

36. The apparatus according to claim 3 wherein the path is circular or straight.

37. The apparatus according to claim 4 wherein the path is circular or straight.

38. The apparatus according to claim 5 wherein the path is circular or straight.

39. The apparatus according to claim 6 wherein the path is circular or straight.

40. The apparatus according to claim 7 wherein the path is circular or straight.

41. The apparatus according to claim 8 wherein the path is circular or straight.

42. The apparatus according to claim 17 wherein the path is circular or straight.

43. The apparatus according to claim 25 wherein the path is circular or straight.

44. A tomography apparatus comprising:
means for support of an object to be subjected to tomography;
means for providing a source of radiation having a focal spot; and
means for detecting the radiation; and
means for carrying the focal spot along a path relative to the means for support during a tomography operation, wherein the means for carrying comprises means for prompting a relative shift of the focal spot with respect to one end of the means for carrying;
wherein the means for prompting the relative shift comprises means for causing relative motion that is cycloid epicycloid or hypocycloid.

45. The apparatus according to claim 44 wherein the means for prompting the relative shift comprises means for motion mounted at the end of the means for carrying and provided with an off-centered pin, a position in rotation of the means for motion being indexed to a position of the means for carrying, the pin being engaged in a housing of the means for providing a source of radiation and driving the means for providing a source of radiation in motion relative to the end of the means for carrying.

46. The apparatus according to claim 45 wherein the pin is circular cylindrical with an axis set up on the periphery of the means for motion.

47. The apparatus according to claim 45 wherein the means for prompting the relative shift comprises two motion wheels mounted at the end of the means for carrying, each being provided with an off-centered pin, the positions in rotation of the two wheels being identically indexed on a position of the means for carrying, the pins being engaged in two housings of the means for providing a source of radiation, the two housings being aligned in a main direction of radiation of the means for providing a source of radiation.

48. The apparatus according to claim 46 wherein the means for prompting the relative shift comprises two motion wheels mounted at the end of the means for carrying, each being provided with an off-centered pin, the positions in rotation of the two wheels being identically indexed on a position of the means for carrying, the pins being engaged in two housings of the means for providing a source of radiation, the two housings being aligned in a main direction of radiation of the means for providing a source of radiation.

49. The apparatus according to claim 47 wherein the two motion wheels are driven by a same driving wheel.

50. The apparatus according to claim 48 wherein the two motion wheels are driven by a same driving wheel.

51. The apparatus according to claim 44 comprising a counterweight mechanism to balance the relative motion of the means for providing a source of radiation.

52. The apparatus according to claim 45 comprising a counterweight mechanism to balance the relative motion of the means for providing a source of radiation.

53. The apparatus according to claim 46 comprising a counterweight mechanism to balance the relative motion of the means for providing a source of radiation.

54. The apparatus according to claim 47 comprising a counterweight mechanism to balance the relative motion of the means for providing a source of radiation.

55. The apparatus according to claim 48 comprising a counterweight mechanism to balance the relative motion of the means for providing a source of radiation.

56. The apparatus according to claim 49 comprising a counterweight mechanism to balance the relative motion of the means for providing a source of radiation.

57. The apparatus according to claim 50 comprising a counterweight mechanism to balance the relative motion of the means for providing a source of radiation.

58. The apparatus according to claim 51 wherein the counterweight mechanism comprises a balancing wheel mounted at the end of an arm for supporting the source of radiation and provided with an off-centered means driving a counterweight, the positions in rotation of a motion wheel and of the balancing wheel being indexed in phase opposition to a position of the means for carrying.

59. The apparatus according to claim 51 wherein the counterweight mechanism comprises a balancing wheel mounted at the end of an arm for supporting the source of radiation and provided with an off-centered means driving a counterweight, the positions in rotation of a motion wheel and of the balancing wheel being indexed in phase opposition to a position of the means for carrying.

60. The apparatus according to claim 52 wherein the counterweight mechanism comprises a balancing wheel mounted at the end of an arm for supporting the source of radiation and provided with an off-centered means driving a counterweight, the positions in rotation of a motion wheel and of the balancing wheel being indexed in phase opposition to a position of the means for carrying.

61. The apparatus according to claim 53 wherein the counterweight mechanism comprises a balancing wheel mounted at the end of an arm for supporting the source of radiation and provided with an off-centered means driving a counterweight, the positions in rotation of a motion wheel and of the balancing wheel being indexed in phase opposition to a position of the means for carrying.

62. The apparatus according to claim 54 wherein the counterweight mechanism comprises a balancing wheel mounted at the end of an arm for supporting the source of radiation and provided with an off-centered means driving a counterweight, the positions in rotation of a motion wheel and of the balancing wheel being indexed in phase opposition to a position of the means for carrying.

63. The apparatus according to claim 55 wherein the counterweight mechanism comprises a balancing wheel mounted at the end of an arm for supporting the source of radiation and provided with an off-centered means driving a counterweight, the positions in rotation of a motion wheel and of the balancing wheel being indexed in phase opposition to a position of the means for carrying.

64. The apparatus according to claim 56 wherein the counterweight mechanism comprises a balancing wheel mounted at the end of an arm for supporting the source of radiation and provided with an off-centered means driving a counterweight, the positions in rotation of a motion wheel and of the balancing wheel being indexed in phase opposition to a position of the means for carrying.

65. The apparatus according to claim 57 wherein the counterweight mechanism comprises a balancing wheel mounted at the end of an arm for supporting the source of radiation and provided with an off-centered means driving a counterweight, the positions in rotation of a motion wheel and of the balancing wheel being indexed in phase opposition to a position of die means for carrying.

66. The apparatus according to claim 44 wherein to modify a mean orientation of irradiation of a source of radiation relative to an envelope of the means for providing a source of radiation, during the tomography operation, a position of a collimator slit is modified in a direction opposite that of the motion of the means for providing a source of radiation.

67. The apparatus according to claim 45 wherein to modify a mean orientation of irradiation of a source of radiation relative to an envelope of the means for providing a source of radiation, during the tomography operation, a position of a collimator slit is modified in a direction opposite that of the motion of the means for providing a source of radiation.

68. The apparatus according to claim 46 wherein to modify a mean orientation of irradiation of a source of radiation relative to an envelope of the means for providing a source of radiation, during the tomography operation, a position of a collimator slit is modified in a direction opposite that of the motion of the means for providing a source of radiation.

69. The apparatus according to claim 47 wherein to modify a mean orientation of irradiation of a source of radiation relative to an envelope of the means for providing a source of radiation, during the tomography operation, a position of a collimator slit is modified in a direction opposite that of the motion of the means for providing a source of radiation.

70. The apparatus according to claim 48 wherein to modify a mean orientation of irradiation of a source of radiation relative to an envelope of the means for providing a source of radiation, during the tomography operation, a position of a collimator slit is modified in a direction opposite that of the motion of the means for providing a source of radiation.

71. The apparatus according to claim 49 wherein to modify a mean orientation of irradiation of a source of radiation relative to an envelope of the means for providing a source of radiation, during the tomography operation, a position of a collimator slit is modified in a direction opposite that of the motion of the means for providing a source of radiation.

72. The apparatus according to claim 50 wherein to modify a mean orientation of irradiation of a source of radiation relative to an envelope of the means for providing a source of radiation, during the tomography operation, a position of a collimator slit is modified in a direction opposite that of the motion of the means for providing a source of radiation.

73. The apparatus according to claim 58 wherein to modify a mean orientation of irradiation of a source of radiation relative to an envelope of the means for providing a source of radiation, during the tomography operation, a position of a collimator slit is modified in a direction opposite that of the motion of the means for providing a source of radiation.

74. The apparatus according to claim 44 wherein the path is circular or straight.

75. The apparatus according to claim 45 wherein the path is circular or straight.

76. The apparatus according to claim 46 wherein the path is circular or straight.

77. The apparatus according to claim 47 wherein the path is circular or straight.

78. The apparatus according to claim 48 wherein the path is circular or straight.

79. The apparatus according to claim 49 wherein the path is circular or straight.

80. The apparatus according to claim 50 wherein the path is circular or straight.

81. The apparatus according to claim 58 wherein the path is circular or straight.

82. The apparatus according to claim 66 wherein the path is circular or straight.

83. A tomography apparatus comprising:

means for support of an object to be subjected to tomography;

means for providing a source of radiation having a focal spot; and means for detecting the radiation; and means for modifying a mean orientation of irradiation of the means for providing the source of radiation relative to a housing of the means for providing a source of radiation, during the tomography operation;

wherein the means for prompting the relative shift comprises means for causing relative motion that is cycloid, epicycloid or hypocycloid.

84. The apparatus according to claim 83 wherein to modify a mean orientation of irradiation of a source of radiation relative to an envelope of the means for providing a source of radiation, during the tomography operation, a position of a collimator slit is modified in a direction opposite that of the motion of the means for providing a source of radiation.

85. The apparatus according to claim 83 comprising a counterweight mechanism to balance the relative motion of the means for providing a source of radiation.

86. The apparatus according to claim 83 wherein a path of the focal spot relative to the means for support is circular or straight.

87. The apparatus according to claim 44, wherein the means for prompting the relative shift is capable of causing relative motion that is cycloid, epicycloid or hypocycloid.

88. The apparatus according to claim 83, wherein the means for prompting the relative shift is capable of causing relative motion that is cycloid, epicycloid or hypocycloid.

* * * * *

UNITED STATES PATENT AND TRADEMARK OFFICE
CERTIFICATE OF CORRECTION

PATENT NO.       : 7,212,606 B2
APPLICATION NO.  : 11/180266
DATED            : May 1, 2007
INVENTOR(S)      : Henri Souchay, Remy Klausz and Matti Petri Jouhikainen It is certified that error appears in the above-identified patent and that said Letters Patent is hereby corrected as shown below:

Column 10, line 52, delete "mourned" and insert --mounted--, therefor.
Column 14, line 30, delete "die" and insert --the--, therefor.

Signed and Sealed this
Twenty-ninth Day of May, 2012

David J. Kappos
*Director of the United States Patent and Trademark Office*